US 6,601,457 B2

(12) United States Patent
Li et al.

(10) Patent No.: US 6,601,457 B2
(45) Date of Patent: Aug. 5, 2003

(54) TEXTILE FABRIC TESTING

(75) Inventors: Yi Li, Kowloon (HK); Jun Yan Hu, Kowloon (HK); Hes Lubos, Liberec (CZ)

(73) Assignee: The Hong Kong Polytechnic University, Kowloon (HK)

( * ) Notice: Subject to any disclaimer, the term of this patent is extended or adjusted under 35 U.S.C. 154(b) by 0 days.

(21) Appl. No.: 09/901,579

(22) Filed: Jul. 11, 2001

(65) Prior Publication Data

US 2003/0010133 A1 Jan. 16, 2003

(51) Int. Cl.[7] .............................. G01N 3/08; G01N 19/02
(52) U.S. Cl. ................................................. 73/818; 73/9
(58) Field of Search ........................ 73/824, 818, 815, 73/159, 9

(56) References Cited

U.S. PATENT DOCUMENTS

| 4,936,135 | A | * | 6/1990 | Annis et al. ...................... 73/7 |
| 5,297,062 | A | * | 3/1994 | Cresson et al. ............. 162/198 |
| 5,557,039 | A | * | 9/1996 | Annis et al. ...................... 73/7 |
| 5,563,329 | A | * | 10/1996 | Smith et al. ................ 73/12.01 |
| 5,689,058 | A | * | 11/1997 | Yuan ............................... 73/9 |
| 5,795,989 | A | * | 8/1998 | Simmons et al. ................ 73/7 |
| 5,795,990 | A | * | 8/1998 | Gitis et al. ...................... 73/10 |

FOREIGN PATENT DOCUMENTS

JP        58167960 A   * 10/1983   .......... G01N/33/36

* cited by examiner

*Primary Examiner*—Hezron Williams
*Assistant Examiner*—Lilybett Martir
(74) *Attorney, Agent, or Firm*—Leydig, Voit & Mayer, Ltd.

(57) ABSTRACT

A single fabric testing apparatus is capable of measuring mechanical and thermal characteristics of a specimen previously carried out in separate testing apparatuses. The single apparatus is provided with a plurality of mechanical and temperature sensors and a heatable top plate. In use, a ram moves the top plate vertically downwards to press a fabric specimen against a bottom plate. The plate is surrounded by a fixed upstanding peripheral skirt against which an outer periphery of the specimen is bent to enable shearing and bending characteristics to be measured. The bottom plate is biased upwards by a spring which is compressed until the top plate is arrested by a fixed frame member. Further downward movement of the ram enables compressibility of the specimen to be determined. A rotatable section of the top plate can be turned by a stepping motor to determine the surface friction characteristics of the specimen.

7 Claims, 4 Drawing Sheets

Upper Measuring Head

Bending Measuring Head

Signal of Bending and Shearing

Signal of Pressure

Impulse of Heatflux

Signal of Heatflux

Signal of Friction

TEXTILE FABRIC TESTING

BACKGROUND OF THE INVENTION

1. Field of the Invention

The invention relates to textile fabric testing.

2. Description of the Prior Art

Many factors are commonly assessed when preparing and testing textile fabrics. Broadly stated, these factors include simulating and measuring mechanical and thermal sensory signals and psychological judgement processes during human hand evaluation of textiles. At present instruments or apparatuses are available to test the appropriate factors separately which means the overall costs are relatively high and difficulties are encountered in interpreting the test results because different instant conditions will prevail in the separate tests.

SUMMARY OF THE INVENTION

It is an object of the invention to overcome or at least reduce this problem.

According to the invention there is provided a single apparatus for testing planar textile fabric specimens, the apparatus comprising an upwardly biased horizontal bottom plate surrounded by a peripheral vertically fixed upstanding skirt that defines an upward facing cross-sectional area that is smaller than a cross-sectional area of the specimen, a movable horizontal top plate having cross-sectional area that is less than the upward facing cross-sectional area, a ram, for moving the top plate up and down vertically during each test cycle relative to the bottom plate, which is arranged to bend the specimen at its periphery against the skirt while pressing a central region of the specimen against the bottom plate, in which the bottom plate is arranged to be vertically arrested to allow the ram to cause the top plate to compress the central region of the specimen against the bottom plate, including mechanical sensors to monitor the prevailing mechanical conditions during each test cycle to determine the thickness of the specimen, and shearing and bending characteristics and compressibility of the specimen.

The top plate preferably has a rotatable auxiliary section within its cross-sectional area, a motor to rotate the section about a vertical axis when the section is pressed against a top surface of the specimen and mechanical sensors for monitoring the operation of the motor to determine frictional resistance to rotation of the section caused by the specimen.

The top plate may be heated and maintained at a temperature greater than environmental temperature, and sensors provided to monitor the prevailing temperature conditions heat fluxes during each test cycle.

The apparatus may be mounted in a cabinet during use to enable the environmental conditions of the apparatus to be maintained constant and independent of prevailing environmental changes outside the cabinet.

BRIEF DESCRIPTION OF THE DRAWINGS

An apparatus for testing a planar textile fabric specimen according to the invention will now be described by way of example with reference to the accompanying drawings in which.

DESCRIPTION OF THE PREFERRED EMBODIMENTS

Figure 1:
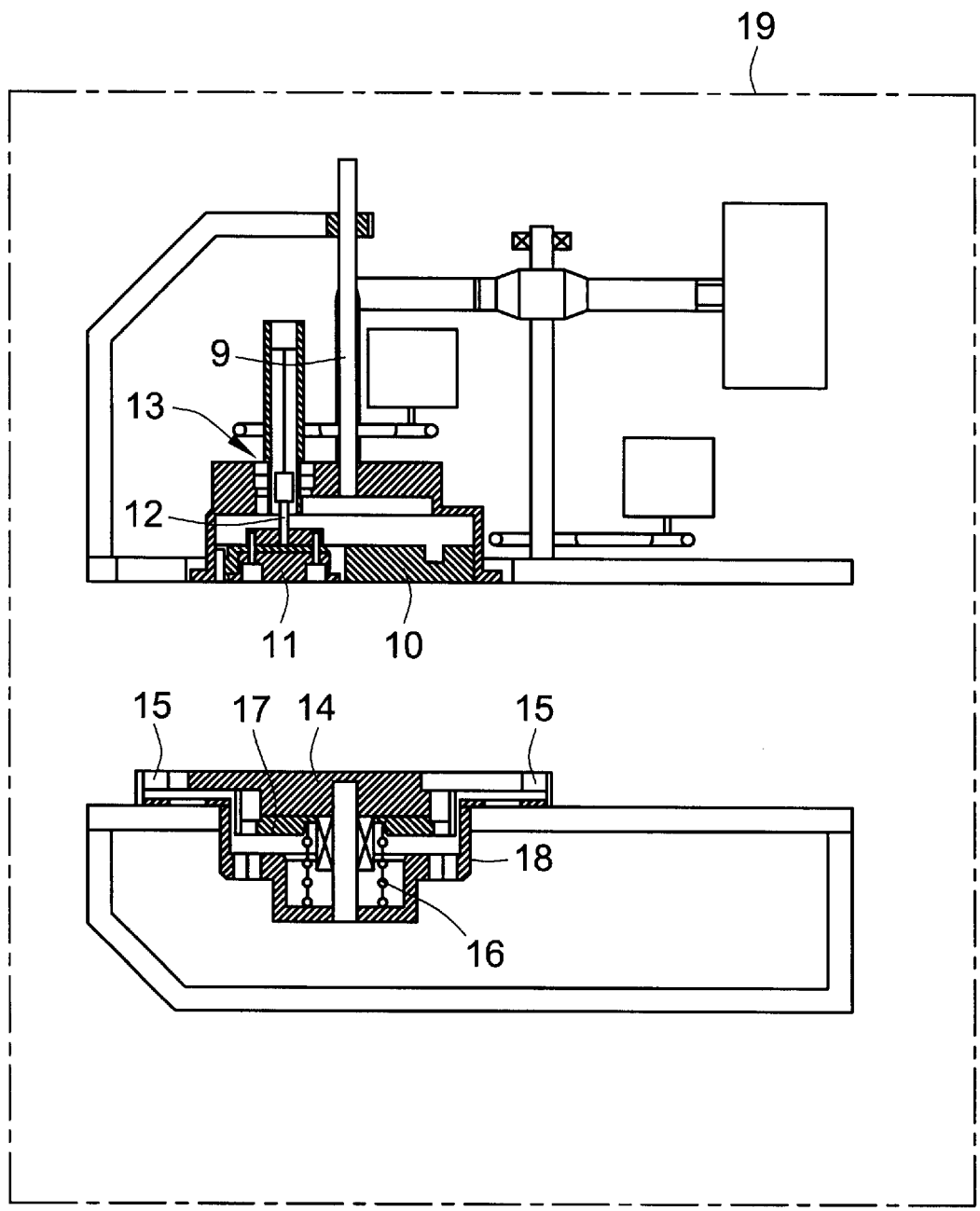
FIG. 1 is an overall schematic sectional elevation of the apparatus.

Referring to the drawings, the apparatus is devised to apply forces to and to compress a specimen while measuring the mechanical and temperature conditions prevailing, using generally well-known sensors, and supplying signals generated and prevailing during each test cycle to a central controller (not shown). The controller is programmed to calculate factors typically required for assessing characteristics of textile fabrics.

Overall in FIG. 1, a vertical ram 9 supports an upper planar measuring head plate 10 that contains a friction measuring unit 11, formed by a rotatable section of the plate 10, coupled to a vertical shaft 12 that is driven by a stepping motor 13. The plate 10 is heated and maintained at a temperature of a normal human hand. This is typically 10° C. above the environmental temperature.

Figure 2:
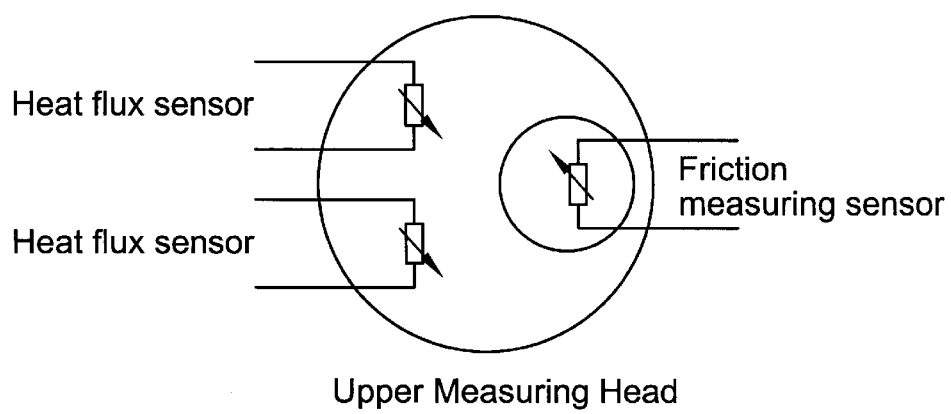
FIG. 2 is a schematic plan view of an upper measuring head.
Figure 3:
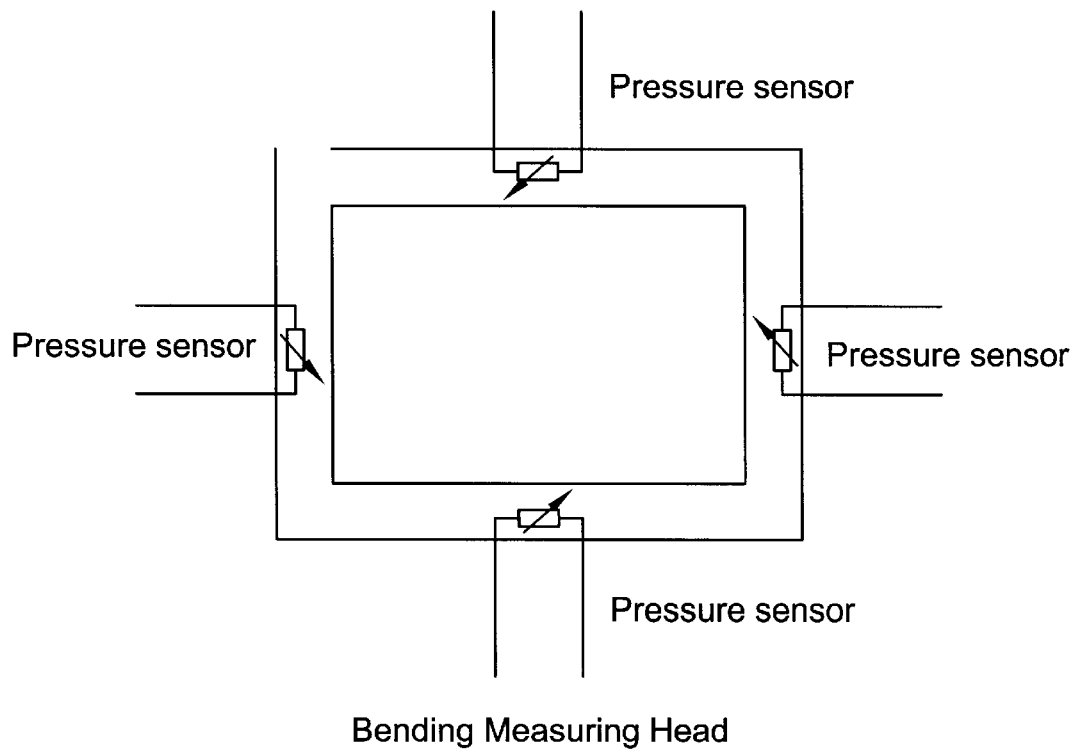
FIG. 3 shows schematically a plan view of a bending measuring frame.

A lower planar measuring head plate 14 is supported below the plate 10 and heat flowing from the top plate towards the bottom plate is determined during testing (see layout in FIG. 2). The lower plate 14 is surrounded by an upstanding skirt 15 providing a pressure sensing frame (see FIG. 3) for determining shearing and bending characteristics of the specimen, as explained below. In the apparatus described, both upper and lower plates 10 and 12 have a surface cross-sectional area of 112×112 mm with rounded edges, and a fabric specimen having dimensions of 120×120 mm is used. The specimen is initially placed symmetrically over the lower plate 14 with its peripheral edges extending over and evenly beyond the skirt 15. The top surface of the lower plate 14 is supported at least approximately the same height as the top surface of the skirt 15.

In carrying out a test cycle, the ram 9 is moved down to press the specimen downwards against the skirt 15. At this point the specimen is gripped between the upper plate 10 and the lower plate 14. It is also at this point that (extra) downward resistance is first experienced by the ram 9 and this may be used to take a measurement of the thickness of the specimen. In other words, the travel of the ram to press the upper plate directly against the lower plate being known, a distance (less than the travel) at which resistance is first experienced represents a thickness of the specimen.

A spring 16 upwardly biases a platform 17 on which the lower plate 14 is mounted. As the ram moves downwards to press the specimen against the lower plate 14, edges of the specimen begin to bend enabling bending forces to be measured, while taking into account the force required to compress the spring 16.

The ram 9 continues to move down until the platform 17 is pressed against a fixed frame member 18. Force experienced by the ram thereafter enables the compressibility of the specimen to be determined. It will be appreciated that compressibility could be determined by arresting downward movement of the lower plate in other ways, such as manually or electro-magnetically inserting suitable blocks or stops, if preferred.

The stepping motor 13 can be turned ON to turn the section 11 against the specimen to enable the surface friction of the sample to be determined at any suitable stage of the ram movement.

The above test cycle is then normally repeated after the upper plate 10 has been raised and the specimen turned through 45°. Four different rotational positions of the specimen are usually required to complete a comprehensive test.

Figure 5:
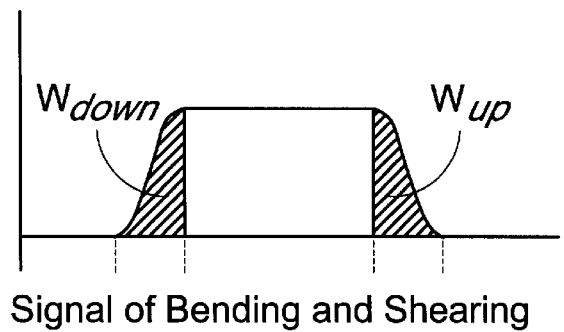
FIG. 5 is a bending and shearing graph for a test cycle.

The apparatus can typically provide the following information:

Bending and Shearing (see FIG. 5)

1) Max/Min/Mean for signal(N) and slope
2) Work(N.s)

$$W_{down} = \int_1^2 (S_{bs} - S_{t1}) dt$$

$$W_{up} = \int_3^4 (S_{bs} - S_{t4}) dt$$

$W_{down}$: work of head down stages;
$W_{up}$: work of head up stage;
$S_{bs}$: Signal of bending and shearing;
$S_{t1}$: Signal at time$_{t1}$;
$S_{t4}$: Signal at time$_{t4}$.

Figure 6:
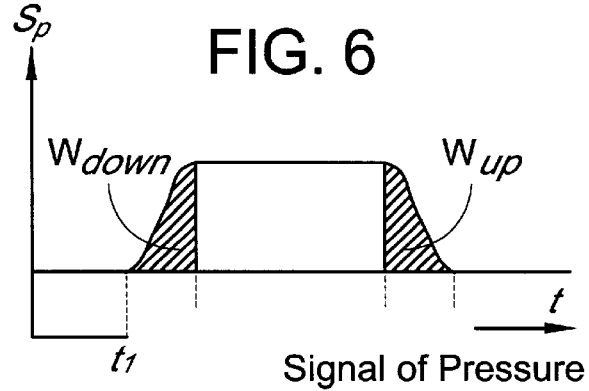
FIG. 6 is a mechanical pressure graph for a test cycle.

Pressure (see FIG. 6)

1) Max/Min/Mean for signal(N) and slope
2) Work(N.s)

$$W_{down} = \int_1^2 (S_p - S_{t1}) dt$$

$$W_{up} = \int_3^4 (S_p - S_{t4}) dt$$

$W_{down}$: work of head down stages;
$W_{up}$: work of head up stage;
$S_p$: Signal of bending and shearing;
$S_{t1}$: Signal at time$_{t1}$;
$S_{t4}$: Signal at time$_{t4}$. (see FIG. 2)

Figure 7:
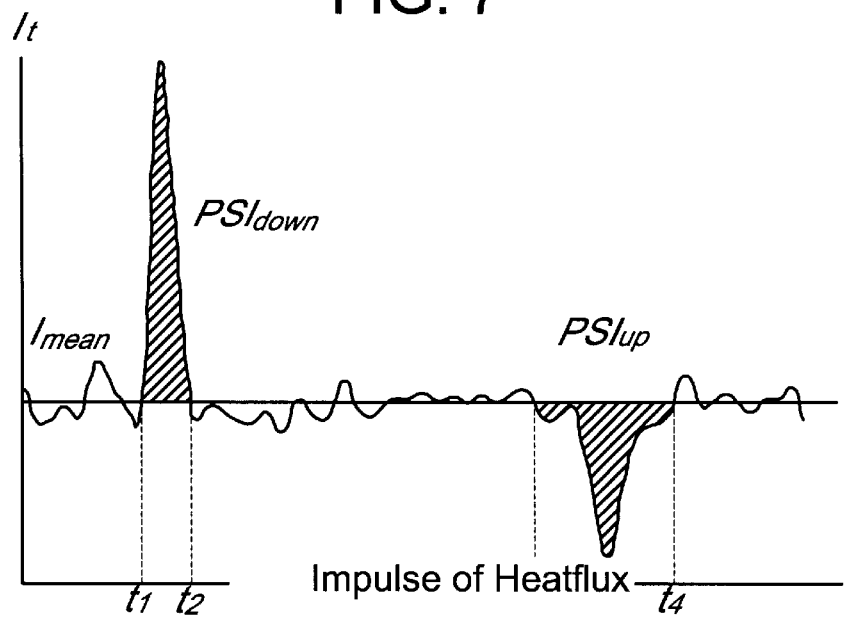
FIG. 7 is an impulse of heat flux graph for a test cycle.
Figure 8:
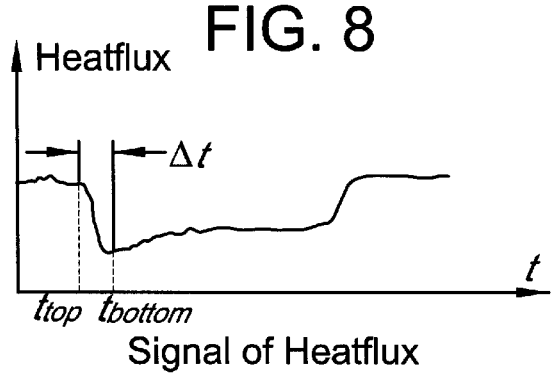
FIG. 8 is a heat flux signal.

Heatflux (see FIGS. 7 and 8)

1) Max/Min/Mean for signal(kw/m$^2$) and slope
2) PSI $$PSI_{down} = \int_1^2 (I_t - I_{mean}) dt$$

$$PSI_{up} = \int_3^4 |I_t - I_{mean}| dt$$

Figure 4:
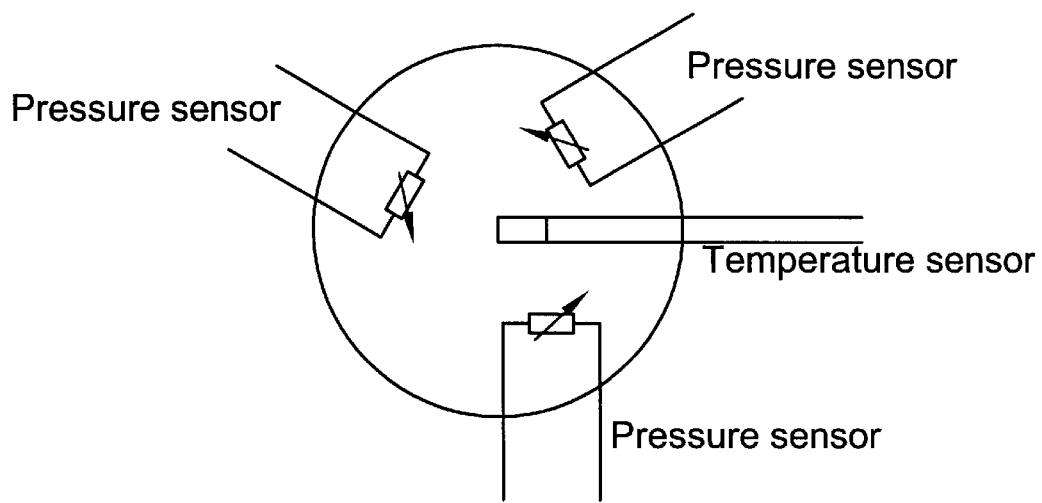
FIG. 4 shows schematically plan view of a lower measuring head.

$PSI_{down}$: PSI of head down stage;
$PSI^{up}$: PSI of head up stage;
$I_t$: Impulse;
$I_{mean}$: Mean of Impulse 3) $\Delta T(S)$ (See FIG. 4)

$$\Delta t = t_{bottom} - t_{top}$$

Figure 9:
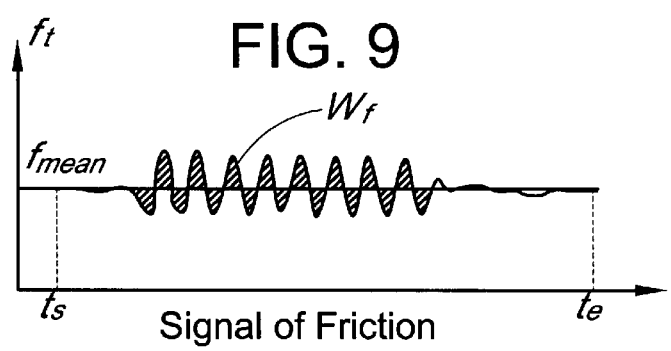
FIG. 9 is a surface friction graph plotted against time.

Friction (see FIG. 9)

1) Max/Min/Mean for signal(N) and slope
2) Work(N.s)

$$W_f = \int_3^{te} |f_1 - f_{mean}| dt$$

$W_f$: work of friction;
$f_1$: friction;
$f_{mean}$: mean of friction;

$T_s$: time of start point;
$t_e$: time of end point (See FIG. 5)

3) Peak Value(N)
   i) Plus: Max/Min
   ii) Minus: Max/Min

The described apparatus is therefore capable of determining the textile fabric handle parameters including:

Thermal parameters:
Thermal resistance
Thermal conductivity
Thermal diffusivity
Thermal absorptivity (warm—cool feeling)
qmax (Kawabata's warm—cooling feeling)
Psycho-sensory Intensity (PSI)
Mechanical Parameters:
Thickness
Compressibility
Dynamic friction coefficient
Bending rigidity in bias direction
Drape rigidity in bias direction The various sensor signals can be computed to enable the following objectives to be developed:

Calibrate and transform the signals to appropriate scales and meaningful measurements;
Plot and display various measurement curves;
Calculate meaningful indexes from the measurement curves;
Transform the scientific indexes to hand perception values that are understood by consumers by using fuzzy logic on the basis of the psychophysical relationships established through psychophysical experiments;
Provide overall hand values of individual consumers and/or consumer groups from the hand perception values on the basis of the identified preference patterns from consumer studies.
Have learning capability to learn the changes in consumer preferences and/or new consumer groups by using artificial intelligence.

Thus, the described single apparatus is capable of testing textile fabric specimens to determine a multitude of characteristics typically required in this art. The apparatus is usually or preferably surrounded by a suitable, openable cabinet 19. It will be appreciated that such a cabinet will not normally be necessary when the apparatus is used in a well-controlled environment such as a textile testing laboratory.

We claim:

1. An apparatus for testing textile fabric specimens, the apparatus comprising:
   a horizontal bottom plate having a planar surface separated from and surrounded by a peripheral skirt having a planar surface co-planar with the planar surface of the horizontal bottom plate;
   a movable horizontal top plate having a planar surface with an area smaller than an area surrounded by the peripheral skirt;
   a ram moving the top plate vertically relative to the bottom plate, bending a textile fabric specimen relative to the skirt while pressing a central region of the textile fabric specimen against the bottom plate;
   biasing means resiliently biasing the bottom plate toward the top plate and limiting vertical movement of the bottom plate by the ram when the top plate compresses a central region of the textile fabric specimen against the bottom plate so that thickness and compressibility of the textile fabric specimen can be determined; and mechanical sensors mounted at the skirt for determining the thickness of the textile fabric specimen, shearing and bending characteristics of the textile fabric specimen, and compressibility of the textile fabric specimen.

2. The apparatus according to claim 1, including a heater in the top plate for maintaining the top plate at a temperature higher than environmental temperature and temperature sensors for monitoring the temperature during a test of the textile fabric specimen.

3. The apparatus for testing planar textile fabric specimens according to claim 1, including a cabinet in which the apparatus is mounted for controlling the environmental conditions of the apparatus during testing.

4. The apparatus for testing planar textile fabric specimens according to claim 1, wherein the top plate includes a rotatable auxiliary section, a motor for rotating the auxiliary section about a vertical axis when the auxiliary section is pressed against the textile fabric specimen, and motor sensors for monitoring operation of the motor and frictional resistance to rotation of the auxiliary section.

5. An apparatus for testing textile fabric specimens, the apparatus comprising:

an upwardly biased horizontal bottom plate surrounded by a peripheral vertically fixed upstanding skirt that defines an upward facing area that is smaller than an area of a textile fabric specimen;

a movable horizontal top plate having an area smaller than the upward facing area, and a rotatable auxiliary section within the area of the horizontal top plate;

a motor to rotate the auxiliary section about a vertical axis when the auxiliary section is pressed against the textile fabric specimen;

motor sensors for monitoring operation of the motor and frictional resistance to rotation of the auxiliary section;

a ram for moving the top plate up and down vertically relative to the bottom plate during each test cycle, the ram bending the textile fabric specimen at its periphery against the skirt while pressing a central region of the textile fabric specimen against the bottom plate, the bottom plate being vertically arrested for compression of a central region of textile fabric specimen against the bottom plate by the top plate; and mechanical sensors for monitoring of mechanical conditions during each test cycle for determining thickness of the textile fabric specimen, shearing and bending characteristics of the textile fabric specimen, and compressibility of the textile fabric specimen.

6. The apparatus according to claim 5, including a heater in the top plate for maintaining the top plate at a temperature higher than environmental temperature and temperature sensors for monitoring the temperature during a test of the textile fabric specimen.

7. The apparatus for testing planar textile fabric specimens according to claim 5, including a cabinet in which the apparatus is mounted for controlling the environmental conditions of the apparatus during testing.

* * * * *